United States Patent [19]

Ohashi et al.

[11] Patent Number: 5,241,002
[45] Date of Patent: Aug. 31, 1993

[54] ANIONIC LIVING POLYMERS, THEIR DERIVATIVES AND COMPOSITION COMPRISING THEM

[75] Inventors: Yuji Ohashi, Sakura; Masataka Ooka, Sakai, both of Japan

[73] Assignee: Dainippon Ink And Chemicals, Ltd., Tokyo, Japan

[21] Appl. No.: 845,577

[22] Filed: Mar. 4, 1992

Related U.S. Application Data

[62] Division of Ser. No. 711,780, Jun. 7, 1991, Pat. No. 5,194,547.

[30] Foreign Application Priority Data

Jun. 8, 1990 [JP] Japan .................. 2-148662

[51] Int. Cl.$^5$ .............. C08F 8/30; C08F 216/38; C08F 8/32
[52] U.S. Cl. ............. 525/123; 526/315; 526/316; 525/124; 525/328.6; 525/328.7; 525/379; 525/162
[58] Field of Search ............................ 525/123

[56] References Cited

U.S. PATENT DOCUMENTS 3,625,926 12/1971 Dowbenko .
3,637,760 1/1972 Dowbenko .
4,056,580 11/1977 Lochmann et al. .
4,246,370 1/1981 Lewis et al. .
4,503,175 3/1985 Houze et al. .................. 524/39

FOREIGN PATENT DOCUMENTS 61-261368 11/1986 Japan .

*Primary Examiner*—Joseph L. Schofer
*Assistant Examiner*—Wu C. Cheng
*Attorney, Agent, or Firm*—Armstrong, Westerman, Hattori, McLeland & Naughton

[57] ABSTRACT

The methacrylic ester polymers produced according to this invention are uniquely distinguished from the radically prepared polymers of similar composition by the fact that both polymers produced: by anionic living polymerization and by deactivating the active terminals of anionic living polymers; contain acetal and/or ketal groups as the blocked hydroxyl groups and have narrow molecular weight distribution. Hydroxyl group-containing methacrylic acid ester polymers are produced by hydrolysis of the above-mentioned polymers. The anionic living polymers are produced in high yields by anionically polymerizing methacrylic acid esters containing an acetal or ketal group in the presence of initiators such as alkaline metal alkoxides. The polymers of the present invention can be used in various fields of applications such as coatings and adhesives. The polymers of the present invention yield curable high solids compositions.

4 Claims, 1 Drawing Sheet

ANIONIC LIVING POLYMERS, THEIR DERIVATIVES AND COMPOSITION COMPRISING THEM

This is a division of application Ser. No. 711,780 filed Jun. 7, 1991 U.S. Pat. No. 5,194,547 filed Mar. 16, 1993.

FIELD OF THE INVENTION

Anionic living polymers, their derivatives and composition comprising them. These polymers are useful as constituent materials in a wide variety of products ranging from paints, adhesives, molding materials and printing materials.

The composition is useful as paints and adhesives.

BACKGROUND OF THE INVENTION

This invention relates to new and novel anionic living polymers and their derivatives. More specifically, it relates to anionic living polymers produced from methacrylic acid esters having acetal or ketal group and derivatives therefrom.

This invention relates to new and novel curable composition containing these polymers.

There has been no report of producing anionic living polymers directly from methacrylic acid ester monomers, containing at least one hydroxyl group within one molecule, because of presence of active hydrogen within the methacrylic acid ester itself.

The known method for obtaining polymers of hydroxyl group-containing methacrylic acid ester based on anionic polymerization is as follows (JPA 1986-250011):

As a precursor for a polymer of a hydroxyl group-containing methacrylic ester, an anionic living polymer having protected hydroxyl groups is produced by polymerizing methacrylic acid ester having a substituted silyl group-protected hydroxyl group (that is, the hydroxyl group is protected by a substituted silyl group as a silyloxy group) in the presence of an anionic polymerization initiator.

However, the yield of an anionic living polymer is very low when such methacrylic acid ester having silyl group-protected hydroxyl group is anionically polymerized using potassium tert-butoxide as a polymerization initiator (referred to as initiator).

Evidence for such problem was published in "YUKI-GOUSEI KAGAKU KYOUKAISI (JAPAN)", page 147, vol. 44, 1986, which reported, in part, that anionic polymerization using methacrylic acid ester with silyl group-protected was inefficient.

SUMMARY OF INVENTION

One of the objectives of the present invention is to present an anionic living polymer produced from methacrylic acid ester having a protected hydroxyl group with the use of the conventional technology of adding metal alkoxide as an anionic initiator.

In addition, it is possible to expand application possibilities of the present invention by presenting methacrylic acid ester polymers having a protected hydroxyl group produced by deactivating the active terminals of the anionic living polymers. Further object of the present invention is to present hydroxyl group-containing polymers of methacrylic acid esters by hydrolyzing reaction of the methacrylic acid ester polymers having a protected hydroxyl group under acidic condition.

Further objectives of the present invention is to provide a curable composition comprising a compound having at least two functional group reactive with hydroxyl groups and the above polymers having a protected hydroxyl group or a hydroxyl group.

BRIEF DESCRIPTION OF THE DRAWINGS

The reference numerals indicate respectively:
1—constant pressure dripping funnel
2—recirculating cooling tubes
3—3-way stopcock

DETAILED EXPLANATION OF THE PRESENT INVENTION

Intensive theoretical and experimental efforts focussing on the above stated objectives has culminated in the present invention in which anionic living polymers having acetal or ketal group, as intermediate polymers for hydroxyl group-containing polymers, can be produced efficiently by anionic polymerization of methacrylic acid esters having protected hydroxyl group as acetal or ketal structure.

That is, this invention presents anionic living polymers produced from methacrylic acid esters having at least one acetal or ketal group. In addition, this invention presents methacrylic acid ester polymers, having acetal or ketal groups in the side chain, which is produced by deactivating the active terminals of the above anionic living polymers.

In order to prepare anionic above-described living polymers of methacrylic acid ester having at least one acetal or ketal group in a molecule, the following procedures can be adopted as an example:

(i) homopolymerization of a methacrylic acid ester having at least one acetal and/or ketal group in a molecule (referred to as methacrylic acid ester (B)) which is formally derived from a methacrylic acid ester having at least one hydroxyl group in a molecule (referred to as methacrylic acid ester (A)) by blocking the said hydroxyl group in shape of introducing as an acetal and/or ketal structure into methacrylic acid ester (A).

(ii) copolymerization of two or more methacrylic acid esters (B), or (iii) copolymerization of one or more methacrylic acid ester (B) with one or more plain methacrylic acid ester which does not contain neither acetal, ketal nor active hydrogen atom (methacrylic acid ester (C)).

It is sufficient that the hydroxyl group is protected as acetal or ketal structure in said methacrylic acid ester (B), and it is not necessary to produce said ester (B) from ester (A).

That is, it is possible to produce compound (B) by starting with compound (A) itself and protecting the hydroxyl group as acetal or ketal structure; or by starting separately with hydroxyl group-containing acetal and hydroxyl group-containing ketal and converting them to methacrylic acid esters.

There are many procedure for protecting the hydroxyl group in methacrylic acid ester (A) in shape of acetal or ketal structure. Representative examples may include: alcohol exchange reaction between compound (A) and acetal or ketal compounds; reaction between compound (A) with α-halogenoether compounds; reaction between compound (A) and α,β-ethylenically unsaturated ether compounds; and reaction between compound (A) and carbonyl compounds.

Representative examples of hydroxyl group-containing methacrylic acid ester (A) include: β-hydroxyethyl methacrylate, β-hydroxylpropyl methacrylate, dipropyleneglycol monomethacrylate, polyethyleneglycol monomethacrylate or β-hydroxybutyl methacrylate or the like of diol-based monomethacrylate, trimethylolethane methacrylate or trimethylolpropane methacrylate or the like of trivalent or multivalent alcohol-based monomethacrylate; or compounds having polyester structure obtained by reacting above-mentioned hydroxyl group-containing methacrylate with ε-caprolactone.

Further, to mention representative examples of acetal or ketal compounds which can be utilized for preparation of (B) from (A) include: dimethoxymethane, diethoxymethane, 1,1-dimethoxymethane, 1,1-diethoxymethane, 2,2-dimethoxypropane or 2,2-diethoxypropane.

Also, to list representative examples of said α-halogenoether include: chloromethyl methylether, chloromethyl ethylether or benzyl chloromethyl methylether or 2-methoxyethoxymethylchloride and the like chloromethyl ether compounds.

Also, to list representative examples of said α,β-ethylenically unsaturated ether compounds: methyl vinyl ether, ethyl vinyl ether, isobutyl vinyl ether, n-butyl vinyl ether, cyclohexyl vinyl ether and the like alkyl- or cycloalkyl vinyl ether compounds; 2-methoxypropene or 2-ethoxypropane and the like isopropenyl ether compounds; 3,4-dihydro-2H-pyran or 4-methoxy-5,6-dihydro-2H-pyran and the like pyran derivatives sometimes referred to as a cyclic unsaturated ether compounds.

There are many examples of carbonyl compounds, to list only the representative examples: formaldehyde, paraformaldehyde, acetaldehyde, propionaldehyde, butylaldehyde, isobutylaldehyde or benzoaldehyde and the like aldehyde compounds; or acetone, 2-butanone and the like ketone compounds.

Further, to list only the representative examples of hydroxyl group-containing acetal or ketal compounds: 2-(1-ethoxy ethoxy)ethanol, 2-isobuthoxyethoxy)-propanol, 2-tetrahydropyranyloxyethanol, 4-tetrahydropyranyloxybutanol, 6-(1-methoxymethoxy)hexanol, 2-(1-methoxyethoxy)ethanol or 2-(1-methoxyethoxy)-propanol and the like hydroxyl group-containing compounds; or 2-(1-methoxy-1-methylethoxy)propanol, 2,2-dimethyl-1,3-dioxolane-4-yl-methanol or 2-ethyl-2-methyl-1,3-dioxolane-4-yl-methanol and the like hydroxyl group-containing ketal compounds.

Further, to list only the representative examples of compounds used for conversion of hydroxyl group-containing acetal or ketal compounds to methacrylic acid esters (B); methacryloyl chloride or methacryloyl bromide and the like acid halide compounds; or methacrylic anhydride.

The representative examples of methacrylic acid esters (B) prepared by using above materials include various compounds with structures shown below; wherein M represents methacrylol group represented by the structure:

and wherein X represents for example:

—CH$_2$—O—CH$_3$,

—CH$_2$—O—CH$_2$—CH$_3$,

—CH$_2$—O—CH$_2$—C$_6$H$_5$,

—CH$_2$—O—CH$_2$—CH$_2$—O—CH$_3$,

That is, representative examples of those compounds which belong to compound (B) are:

M—O—CH$_2$—CH$_2$—O—X,

M—O(CH$_2$)$_4$O—X,

M—O(CH$_2$)$_6$O—X,

M—O(CH$_2$CH$_2$—O)$_n$X,

Further, all those methacrylic acid esters which possess neither the acetal nor ketal structure, contain no active hydrogen and those which themselves are able to anionically polymerize, can be used as said methacrylic acid esters (C), and the representative examples are: methyl methacrylate, ethyl methacrylate, n-propyl methacrylate, isopropyl methacrylate, n-butyl methacrylate, isobutyl methacrylate, tert-butyl methacrylate, 2-ethylhexyl methacrylate, isodecyl methacrylate, lauryl methacrylate, tridecyl methacrylate or stearyl methacrylate and the like alkyl methacrylate compounds; cyclohexyl methacrylate and the like cycloalkyl methacrylates; 2-ethoxyethyl methacrylate, 2-ethoxypropyl methacrylate, 2-methoxyethyl methacrylate, methoxypolyethyleneglycol methacrylate or tetrahydrofurfuryl methacrylate and the like ether-bond containing methacrylates; 2-(dimethylamino)ethyl methacrylate or 2-(diethylamino)ethyl methacrylate and the like tertiary amino group-containing methacrylates; allyl methacrylate and the like allyl group-containing methacrylates; or benzyl methacrylate or 2-phenylethyl methacrylate and the like aromatic ring-containing methacrylates.

The reaction, between the hydroxyl group-containing methacrylic acid esters (A) and acetal or ketal compounds to produce methacrylic acid esters (B), is carried out generally at room or slightly elevated temperatures for 0.5 to 30 hours and removal of the low boiling-point alcohol out of the system.

Such a reaction can also be carried out in an atmosphere of inert gas or in a solvent, as required. A suitable solvent for this purpose includes benzene, toluene and xylene.

Further, acid catalyst is used in a such reaction. Suitable catalysts include hydrochloric acid, sulfuric acid or nitric acid and the like inorganic acids; p-toluenesulfonic acid, benzene-sulfonic acid or trichloroacetic acid and the like organic acids; or boron trifluoride, potassium hydrogensulfate or phosphorous pentoxide.

In these reactions, it is preferable to add an inhibitor, as necessary, and to list only the well known ones: hydroquinone, 4-methoxyphenol or 4-tert-butylcatechol.

Also, the reaction between the compound (A) and α-halogenoether to produce compound (B) is usually carried out at room temperature or under cooling, for 0.5 to 30 hours in an inert gas atmosphere.

The reaction can be carried out either with or without solvents, and suitable solvents include: tetrahydrofuran, methylene chloride, hexane, heptane or benzene.

Further, these reactions are usually carried out in the presence of a basic compound. Representative examples of such compounds are: diisopropylethylamine or triethylamine and the like amine compounds; and it is entirely permissible to utilize polymerization inhibitors such as hydroquinone or 4-methoxyphenol.

In producing compound (B) from compound (A) and α,β-ethylenically unsaturated ether compounds, this reaction is usually carried out at room or slightly elevated temperatures for 0.5 to 30 hours under an inert gas atmosphere of nitrogen or argon. In this reaction, a solvent is used or not.

Examples of suitable solvents are: methylene chloride, dioxane, tetrahydrofuran, diethyl ether, pentane, hexane, heptane, benzene, toluene or N,N-dimethylformamide.

In this reaction, an acid catalyst is generally used, and representative examples of such catalysts are: p-toluenesulfonic acid, benzenesulfonic acid, trichloroacetic acid or trifluoroacetic acid and the like organic acids; hydrochloric acid, sulfuric acid, phosphorous oxychloride, phosphoric acid or hydrogen bromide and the like inorganic acids; boron trifluorideetherate, aluminum trichloride, zinc chloride, magnesium chloride and other Lewis acids; pyridinium p-toluenesulfonate and other organic acid salts. Further, polymerization inhibitors used in this reaction include: hydroquinone 4-methoxyphenol or 4-tert-butylcatechol.

The reaction to produce compound (B) from (A) with carbonyl compounds is usually carried out at elevated temperatures for 0.5 to 30 hours in an inert gas atmosphere of nitrogen or argon under removal of water. In this reaction, a solvent is used or not. Some examples of solvents are: benzene, toluene or xylene.

In this reaction, catalyst is used, and representative examples of such catalysts are: hydrochloric acid, sulfuric acid, phosphoric acid or hydrogen bromide and or other inorganic acids; p-toluenesulfonic acid or carboxylic acid and other organic acids are some representative examples.

In the preparation of ester (B) from ester (A) and carboxyl compounds, when a methacrylic acid ester containing only one hydroxyl group is used as ester (A) and an alcohol such as methanol or ethanol is also used as a coreactant, an acetal or ketal compound (B) containing only one methacryloyloxy group is obtained.

Additionally, when a methacrylic acid ester having two hydroxyl groups is reacted with carbonyl compounds, if necessary in the presence of above mentioned alcohols, an acetal or ketal compound (B) containing one methacryloyloxy group is obtained.

For these reaction systems with carbonyl compounds, polymerization inhibitors such as hydroquinone, 4-methoxyphenol or 4-tert-butylcatechol can be added beforehand, if desired.

Further, for the production of compound (B) from a hydroxyl group-containing acetal or ketal compound, the reaction of the acetal or ketal compounds with a methacrylic acid halide or methacrylic anhydride is usually carried out at room or elevated temperatures for 0.5 to 30 hours, in an inert gas atmosphere of nitrogen or argon, in the presence of a basic compound such as triethylamine, tributylamine and pyridine.

Further, in this reaction a solvent is used, if necessary, and representative examples of such solvent are: diethyl ether, tetrahydrofuran, hexane, heptane, benzene or toluene.

It is desirable to add to the reaction systems beforehand such polymerization inhibitors as hydroquinone, 4-methoxyphenol or 4-tert-butylcatechol.

As presented above, by converting the hydroxyl group in methacrylic acid esters (A) to an acetal or ketal group, or by esterification of hydroxyl group-containing acetal or ketal compounds to methacrylic acid esters, it is possible to produce the key compound of the present invention, i.e. an intermediate compound (B) which has protected hydroxyl group as acetal or ketal structure.

The compounds (B) itself is reactive to radicals, it is necessary to use a polymerization inhibitor and to preserve it in a dark cool place.

Such polymerization inhibitors are preferably basic compounds, and representative examples are phenothiazine or p-phenylenediamine and the like amine compounds.

The anionic living polymers of the present invention are produced by anionically homopolymerizing compound (B) or by anionically copolymerizing compound (B) with compound (C) which has neither acetal or ketal group nor active hydrogen, in the presence of an anionic initiator.

Compounds suitable as inhibitors are those used in anionic polymerization of methacrylic acid esters having no active hydrogen.

Some representative examples are: potassium tert-butoxide, potassium methoxide, sodium methoxide or lithium tert-butoxide and the like alkaline metal alkoxides; tert-butylmagnesium bromide, or cyclohexylmagnesium bromide and other Grignard reagents; lithium naphthalene, sodium naphthalene or potassium naphthalene and the like alkaline metal salts of naphthalene; lithium biphenyl, sodium biphenyl and other alkaline metal salts of biphenyl; or lithium aluminum hydride, n-butyl lithium, phenyl lithium and other such lithium reagents.

Even when an alkaline metal alkoxide is used as the initiator, methacrylic acid esters (B) containing an acetal or ketal group gives the targeted anionic living polymers having acetal or ketal groups as protected hydroxyl groups in high yields, whereas methacrylic acid esters having a substituted silyl group-protected hydroxyl group gives low yields of anionic living polymers because of side reactions.

The above process forms the core of the inventive steps of the present invention.

In this case of using an alkaline metal alkoxide as an initiator, anionic polymerization is carried out in a temperature range of $-100°$ to $+120°$ C., preferably in the range of $0°$ to $100°$ C., more particularly $50°$ to $100°$ C. for a period ranging from 0.5 to 30 hours.

For initiators other than alkaline metal alkoxides, the polymerization is carried out in a temperature range of $-100°$ to $50°$ C., preferably $-100°$ to $0°$ C., ore particularly $-100°$ to $-50°$ C. for a period ranging from 0.5 to 30 hours.

In the polymerization reaction, it is possible to use solvents such as benzene, toluene or xylene and the like aromatic hydrocarbons; pentane, hexane, heptane or cyclohexane and the like aliphatic or cycloaliphatic hydrocarbons; or tetrahydrofuran or diethyl ether and the like ethers. These solvents can be used alone or in combination with two or more other solvents.

The anionic polymerization is preferably carried out in an atmosphere of nitrogen or argon, and may be carried out under reduced pressure.

The degree of polymerization of the anionic living polymers depends upon the mol ratio of methacrylic acid esters to the initiator, and the degree of polymerization can be altered by varying the mol ratio.

In the anionic polymerization initiated by alkaline metal alkoxides, alcohols such as methanol and ethanol can be utilized as molecular weight-controlling agents.

In conducting such anionic polymerization reactions, methacrylic acid ester can be added to initiator at one time or at two times or by continuous dropping.

By changing the composition of methacrylic acid esters which constitute the compound (B) or (C), anion living polymers with a variety of structures can be obtained. In the case of copolymerizing two or more methacrylic acid esters, polymers having different structures can be obtained depending on polymerization method.

That is, in copolymerization of two or more methacrylic acid esters, it becomes possible to produce anionic living polymers having a particular structure in a particular location of the final product by changing the composition of monomers feeded to the reaction mixtures.

For example, a monomer "b" selected from the compound (B) is polymerized in the presence of an initiator to obtain an anionic living polymer, followed by polymerizing monomer "c" selected from compound (C) to obtain an overall anionic living polymer having the structure of $(b)_p$——$(c)_q$——L (where, p and q represent the degree of polymerization of each monomers and L represents the active terminal); which is the so-called diblock living polymer. Proceeding further, monomer "b" can be again added to the reaction mixtures to add another polymerization step, thereby to produce a polymer having a structure such as $(b)_p$——$(c)_q$——$(b)_r$—L (where, r represents the degree of second polymerization).

The polymers thus obtained has a degree of polymerization in the ranges of 2–1,000, preferably 2–500, and they have active terminal which is stable at relatively low temperatures.

Therefore, the technique of producing anionic living polymers presented in this invention allows an introduction of various polar functional group at the terminal of the molecule by reacting the polymers with various electrophilic reagents.

Further, the active terminal of the anionic living polymers presented in the present invention can be deactivated with the use of an active hydrogen-containing compound such as protonic acid, thereby to produce polymers of methacrylic acid esters with acetal or ketal structure.

Representative examples of such compound used for deactivation are: hydrochloric acid sulfuric acid, trichloroacetic acid, trifluoroacetic acid or p-toluenesulfonic acid and the like protonic acids; methanol, ethanol, propanol. isopropanol or butanol and the like alcohol group; or water.

Polymers of methacrylic acid esters having hydroxyl group can now produced by removing those portions having acetal or ketal structure from the foregoing anionic living polymers whose terminals had been deactivated.

The process of removing those portions having the acetal or ketal structure varies depending on the structure, but in general it is possible to use hydrolysis reaction utilizing acid catalysts.

Representative examples of such acid catalysts are: hydrochloric, sulfuric or nitric acids and the like inorganic acids; p-toluenesulfonic acid, benzenesulfonic acid, methanesulfonic acid, ethanesulfonic acid, trichloroacetic acid or acetic acid and the like organic acids; ion exchange resins having acidic group such as acidic hydroxyl group (—OH), carboxyl group (—COOH) or sulfonic acid group ($—SO_3H$).

The removal reaction of acetal or ketal portions with the use of acid catalysts is usually carried out at room temperature or slightly elevated temperatures for period ranging from 1 minute to 30 hours in water or in mixtures of water and organic solvents. Representative examples of such organic solvents are: methanol, ethanol and the like alcohols; tetrahydrofuran, dioxane or diethyl ether and the like ethers and N,N-dimethylformamide, 1-methyl-2-pyrrolidinone, ethyl acetate, butyl acetate, hexane, heptane, benzene, toluene or xylene. There can be used singly or in combination of two or more solvents.

Since such acid catalysted hydrolysis reactions are equilibrium reactions, the amount of water to be used should be in excess of that of the acetal or ketal group which is to be removed. Such steps can be repeated, as necessary.

Such anionic living polymers, and other polymers obtained by the processes described above (e.g. deactivation treatment, removal of acetal or ketal portions) are distinguished from the conventional polymers of the same composition obtained by the radical polymerization method by two important aspects: ease to control the degrees of polymerization and the narrow range of molecular weight distribution.

Therefore, by making full utilization of these distinguishing characteristics of the present invention, it becomes possible to produce various polymers of the methacrylic acid esters having not only acetal, ketal and hydroxyl groups but also polar functional groups, that were not achievable by the conventional technology.

The polymers of the present invention are characterized by smaller weight-average molecular weights and smaller viscosity-average molecular weight compared with the conventional polymers of the same number-average molecular weight prepared by the radical polymerization method.

Therefore, the various polymers obtained by the anionic polymerization method of the present invention possess lower viscosity and require lesser amount of solvent to achieve a particular viscosity level compared with the conventionally prepared polymers.

Therefore, the anionic living polymers and their derivatives are especially useful as resins for high solid content paints.

Anionic polymers and their derivatives of the present invention can be used to various applications such as high solids coating resins, reactive plasticizers, solubilizers, dispersing agents, emulsifiers, graft polymers, ion exchange resins, macromonomers, thermosetting resins and reactive polymers containing UV-absorbing groups.

An example of the procedure for preparing high solids curable compositions is presented below.

First, an anionic living polymer is diluted with an organic solvent such as xylene, followed by deactivation and hydrolysis by repeated washing with a mixture of an aqueous solution containing an acid such as hydrochloric acid, and an alcohol such as methanol, to produce a solution of a methacrylic acid ester polymer having hydroxyl groups.

The polymer solution is then heated under reduced pressure to distill off low boiling compounds such as water and alcohol, followed by dilution with a solvent such as xylene to obtain a hydroxyl group-containing polymer solution having a specific viscosity.

To this resin solution are added a pigment and a pigment dispersant, and after dispersing the pigment using a paint conditioner, a hardener reactive with hydroxyl groups such as a polyisocyanate is added to give a curable composition.

The composition gives a cured film resistant to water and organic solvents by baking under appropriate conditions.

The curable compositions produced from hydroxyl group-containing polymers of the present invention can be applied in low volatile material content, and thus give cured films having excellent appearance. Moreover, the cured films prepared from the compositions have sufficient crosslinking densities and flexibility necessary for practical use.

Thus, the present invention also present a curable composition comprising (a) a copolymer of methacrylic acid ester having at least one hydroxyl group, which is produced by hydrolyzing an anionic living polymer of a methacrylic acid ester having at least one acetal or ketal group, and (b) a compound having at least two functional groups reactive with hydroxyl groups in each molecule.

Representative examples of the compound having at least two functional groups reactive with hydroxyl groups in each molecule (b) used for the composition of the present invention are polyisocyanates such as hexamethylene diisocyanate, m-xylylene diisocyanate, isophorone diisocyanate, adducts of polyols with diisocyanates and cyclic trimers of diisocyanates; blocked polyisocyanates such as those prepared by blocking the above mentioned polyisocyanates with blocking agents such as lactams, alcohols and oximes; amino resins such as methyl-etherified melamines, butyl-etherified methylol melamines, methyl-etherified benzoguanamines, butyl-etherified benzoguanamines, methyl-etherified methylol ureas and butyl-etherified methylol ureas; poly carboxylic acid anhydrides such as pyromellitic dianhydride and vinyl polymers containing at least two carboxylic anhydride groups in each molecule.

Further, since anionic living polymers of the present invention and polymers obtained by deactivating their active terminals contain protected hydroxyl groups as the structure of acetal or ketal groups, they can therefore be used in combination with a hardener reactive with hydroxyl groups as mentioned above. The composition thus obtained exhibit excellent stability. And if the composition also contain a deblocking catalyst such as an acid, the acetal or ketal groups in the polymers are hydrolyzed with moisture in the air when the composition is applied to a substrate. The resulting hydroxyl group-containing polymer reacts with the hardener to give crosslinked films. Therefore, the composition prepared from the polymer containing acetal or ketal groups, hardeners and deblocking catalyst, if desired, can be utilized as a curable composition having excellent stability.

Thus, the present invention also presents a curable composition comprising (a) a polymer of a methacrylic acid ester having at least one acetal or ketal group which is obtained by deactivation of active terminals of an anionic living polymer, which is produced by anionic polymerization of a methacrylic acid ester having at least one acetal or ketal group, (b) a compound having at least two functional groups reactive with hydroxyl groups in each molecule, and optionally a catalyst.

Representative examples of deblocking catalyst used for the composition of the present invention are inorganic acids such as hydrochloric acid and phosphoric acid; organic acids such as benzenesulfonic acid, p-toluenesulfonic acid, methanesulfonic acid, trichloroacetic acid and mono-or dialkylesters of phosphoric acid; and amine salts of the above-mentioned sulfonic acids.

Furthermore, since anionic living polymers of the present invention and polymers obtained by deactivating their active terminals contain protected hydroxyl groups by acetal or ketal group, they can therefore be used in combination with a hardener of hydroxyl reacting compounds such as polyisocyanate.

Such materials exhibit excellent stability, and when treated with acids as antiprotector, and used in air as paint coating, these materials can react with moisture in the air, and the resulting regenerated hydroxyl group can react with the hardener to provide crosslinking action.

Therefore, such constituents formed by the anitroprotector exhibit excellent stability and can be utilized as reactive resin components.

It has been described in this invention that anionic living polymers are produced in high yields by anionically polymerizing methacrylic acid esters having acetal or ketal groups. A suggested reason for this phenomenon is presented below.

The anionic polymerization of methacrylic acid esters is performed under basic conditions which are conductive to the maintenance of activity of enolate anions.

Acetal and ketal groups are quite stable under basic conditions and are non-reactive with either the above-mentioned enolate anions or anionic initiators. Therefore, the compound (B) can be polymerized to produce anionic living polymers of said compound (B) as in the case of other methacrylic acid esters having no active hydrogens.

Further, the acetal or ketal group has ether linkages, and therefore, each group is quite stable against various nucleophilic reagents and basic reagents. Thus, anionic living polymers can be formed stably without reliance on such special provisions as steric hindrance induced by alkyl substituents such as tert-butyl group.

PREFERRED EMBODIMENTS OF THE PRESENT INVENTION

In this section, the usefulness of the present invention is demonstrated by raising referential, practical and application examples. Unless otherwise stated, percent (%) in the following examples is by weight.

Figure 1:
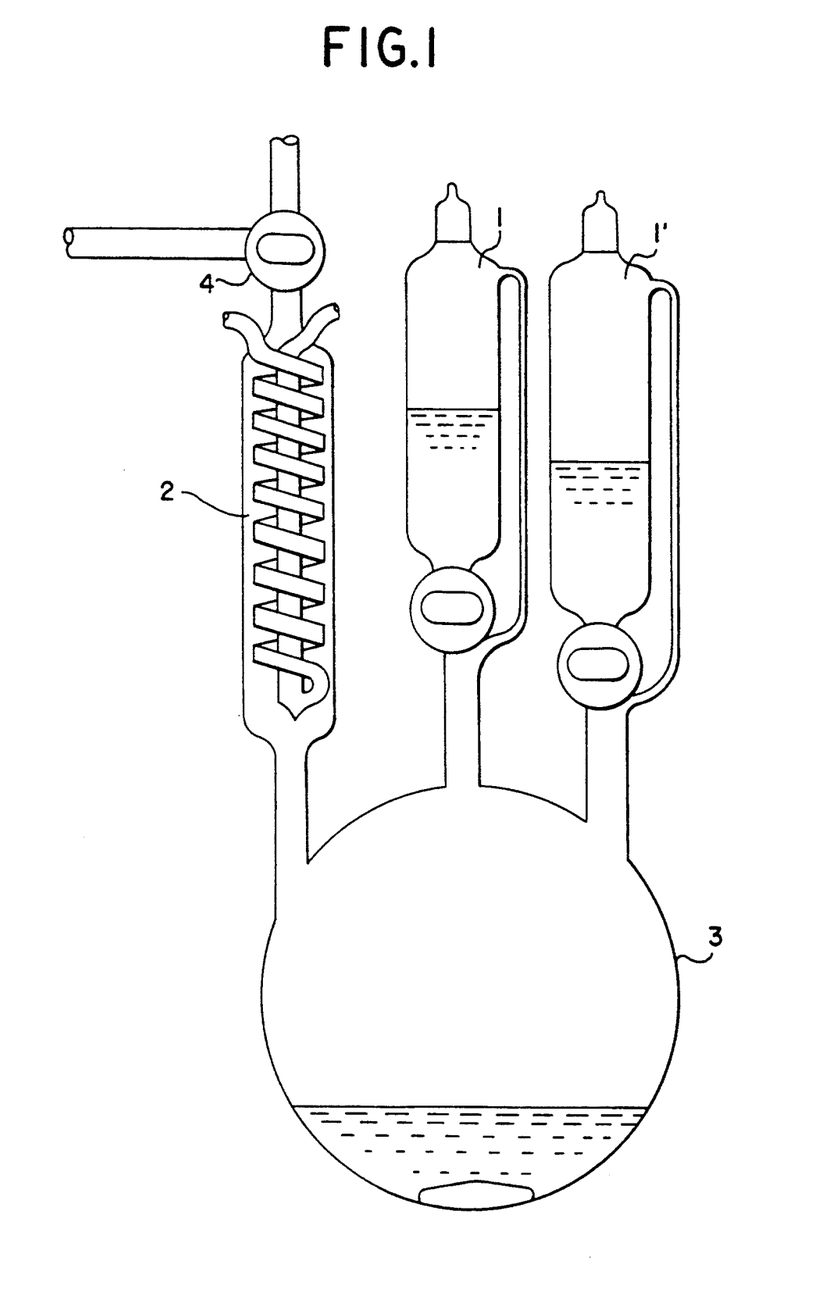
FIG. 1 is a schematic front views of an example apparatus for synthesizing anionic living polymers.

Anionic polymerization experiments were performed in an apparatus shown in FIG. 1, which consists of a 3-way stopcock 4, connected with evacuation and nitrogen lines, a constant pressure dropping funnel 1, a recirculating cooling tube 2, a flask 3 containing an anionic polymerization initiator and a magnetic stirrer. The process consists of the following steps.

The apparatus system is cooled and evacuated. The system is then filled with nitrogen gas.

The above evacuation and filling steps are repeated several times, if desired. When the desired atmosphere is attained, the monomer is dropped into the flask to cause polymerization under desired conditions.

The monomer synthesis was performed in a flask equipped with a nitrogen inlet tube, a thermometer, a stirrer, a cooling tube and a dropping funnel.

REFERENTIAL EXAMPLE 1

Preparation of acetal group-containing monomer

Ethyl vinyl ether was placed in the apparatus and was cooled to below 10° C. while stirring.

Then, a mixture consisting of an equimolar amount of β-hydroxyethyl methacrylate to ethyl vinyl ether and hydrochloric acid (0.3 mol % to ethyl vinyl ether) was added to ethyl vinyl ether at the temperatures below 15° C.

After the addition was completed, the mixture was stirred at room temperatures for 3 hours, and was neutralized with an aqueous solution of potassium hydroxide (50 mol % excess to hydrochloric acid). The white solid of potassium chloride was filtered off and the filtrate was extracted with hexane. The extract was washed with an aqueous solution of potassium carbonate, and dried over anhydrous sodium sulfate.

The above extract was further concentrated under reduced pressure after adding phenothiazine in an amount corresponding to 3% of charged β-hydroxyethyl methacrylate.

The crude product was subjected to vacuum distillation using Vigoureux column to give 2-(1-ethoxyethoxy)ethyl methacrylate (EEEMA) in a yield of 91% based on the charged β-hydroxyethyl methacrylate. The product having a boiling point of 56-58° C. at 0.4 mmHg is hereinafter called methacrylic acid ester (B-1).

After adding phenothiazine (0.1% based on B-1), ester (B-1) was stored under nitrogen in a cool place.

Ester (B-1) was subjected to IR, ¹HNMR and Mass analyses to be confirmed to have the structure shown below.

The results of IR spectroscopy, ¹HNMR and mass spectroscopy were as shown in the following Table 1.

TABLE 1

| IR (neat. cm⁻¹) | MS M⁺ (m/e) | ¹HNMR (290MHz. CDCl₃) δ |
|---|---|---|
| 2980. 2930. 2890. 1720. 1635. 1450. 1380. 1320. 1295. 1170. 1140. 1105. 1085. 1060. 950. 860. 815 | 202 | 6.12(s. 1H). 5.57(s. 1H). 4.74(q. 1H). 4.29(t. 2H). 3.87-3.40(m. 4H). 1.94(s. 3H). 1.30(d. 3H). 1.19(t. 3H) |

REFERENTIAL EXAMPLE 2

Preparation of acetal group-containing monomer

Into the apparatus for monomer synthesis were charged β-hydroxyethyl methacrylate (HEMA) and a methylene chloride solution of pyridinium p-toluenesulfonate (10 mol % to HEMA). Then, 3,4-dihydro-2H-pyran (50 mol % excess to HEMA) was dropped into the mixture while stirring over a period of 5 hours at room temperature. Heat gradually evolved was removed by cooling to maintain the temperature of the reaction mixture below 30° C. When the reaction was completed, hexane was added to precipitate pyridinium p-toluenesulfonate. The precipitated pyridinium p-toluenesulfonate was removed by filtration.

The filtrate was washed with an aqueous potassium carbonate solution and dried over anhydrous sodium sulfate. The hexane solution of the product was further concentrated under reduced pressure after adding phenothiazine (3% of charged HEMA).

The crude product was subjected to vacuum distillation using Vigoureux column to give 2-(2-tetrahydropyranyloxy)ethyl methacrylate (THPEMA) in a yield of 82% based on charged HEMA. The product having a boiling point of 72°-75° C. at 0.5 mmHg is hereinafter called methacrylic acid ester (B-2).

After adding phenothiazine (0.1% based on B-2), the ester (B2) was stored under nitrogen in a cool place.

Ester (B-2) was subjected to IR, ¹HNMR and Mass analyses to be confirmed to have the structure shown below.

The results of IR spectroscopy, ¹HNMR and mass spectroscopy were as shown in the following Table 2.

TABLE 2

| IR (neat. cm⁻¹) | MS M⁻ (m/e) | ¹HNMR (290MHz. CDCl₃) δ |
|---|---|---|
| 2950. 2870. 1720. 1635. 1450. 1320. 1295. 1170. 1130. 1080. 1040. 990. 875. 815 | 214 | 6.14(s. 1H). 5.58(s. 1H). 4.68(t. 1H). 4.42-4.25(m. 2H). 4.00-3.47(m. 4H) 1.97(s. 3H). 1.91-1.45(m. 6H). |

REFERENTIAL EXAMPLE 3

Preparation of acetal group-containing monomer

Isobutyl vinyl ether was charged into the apparatus for monomer synthesis and was cooled to 10° C. under stirring. Then, a mixture of β-hydroxypropyl methacrylate (equimols to isobutyl vinyl ether) and concentrated hydrochloric acid (0.5 mol % to isobutyl vinyl ether) was dropped at temperatures below 15° C. under stirring.

After the addition is completed, the reaction mixture was stirred at room temperature for 3 hours, and was neutralized with an aqueous solution of potassium hydroxide (50 mol % excess to hydrochloric acid used). Then, the white solid of potassium chloride was filtered off, and the filtrate was extracted with hexane. The extract was washed with an aqueous solution of potassium carbonate, and dried over anhydrous sodium sulfate.

The above extract was further concentrated under reduced pressure after adding phenothiazine (3% based on charged β-hydroxypropyl methacrylate). The resulting crude product was subjected to vacuum distillation using Vigoureux column to give 2-(1-isobuthoxyethoxy)propyl methacrylate (IBEPMA) in a yield of 86% based on charged HPMA. The product having a boiling point of 66°-69° C. at 0.4 mmHg is hereinafter called methacrylic acid ester (B-3).

After adding phenothiazine (0.1% based on B-3), the ester (B-3) was stored under nitrogen in a cool place.

Ester (B-3) was subjected to IR, ¹HNMR and Mass analyses to be confirmed to have the structure shown below.

[III]

The results of IR spectroscopy, ¹HNMR and mass spectroscopy were as shown in the following Table 3.

TABLE 3

| IR (neat, cm⁻¹) | MS M⁻ (m/e) | ¹HNMR (290MHz, CDCl₃) δ |
|---|---|---|
| 2950, 2870, 1720, 1635, 1450, 1380, 1325, 1295, 1170, 1140, 1100, 1085, 1045, 1010, 940, 905, 815 | 244 | 6.13(s, 1H), 5.59(s, 1H), 4.80(q, 1H), 4.21-3.95(m, 3H), 3.40-3.12(m, 2H), 1.96(s, 3H), 1.91-1.72(m, 1H), 1.33-1.15(m, 6H), 0.92(d, 6H) |

REFERENTIAL EXAMPLE 4

Preparation of ketal group-containing monomer

Into the apparatus for monomer synthesis were charged 2,2-dimethyl-1,3-dioxolan-4-methanol (DMDOMeOH), toluene, triethylamine (equimols to DMDOMeOH) and phenothiazine (2% of DMDO-MeOH) and the mixture was stirred at room temperature. Methacrylic anhydride (90 mol % of DMDO-MeOH) was dropped into the mixture at room temperature, then the reaction was continued at 110° C. for 10 hours.

The reaction mixture was extracted with hexane, neutralized with an aqueous solution of sodium carbonate, and dried over anhydrous sodium sulfate. After addition of phenothiazine (2% of DMDOMeOH), the extract was concentrated under reduced pressure at 80° C.

The crude product was subjected to vacuum distillation using Vigoureux column to give 2,2-dimethyl-1,3-dioxolane-4-yl-methyl methacrylate in a yield of 64% based on charged DMDOMeOH. The product having a boiling point of 52°-53° C. at 0.45 mmHg is hereinafter called methacrylic acid ester (B-4).

After adding phenothiazine (0.1% based on B-4), ester (B-4) was stored under nitrogen in a cool place. Ester (B-4) was subjected to IR, ¹HNMR and Mass analyses to be confirmed to have the structure shown below.

[IV]

The results of IR spectroscopy, ¹HNMR and mass spectroscopy were as shown in the following Table 4.

TABLE 4

| IR (neat, cm⁻¹) | MS M⁺ (m/e) | ¹HNMR (290MHz, CDCl₃) δ |
|---|---|---|
| 2980, 2930, 2880, 1720, 1635, 1450, 1370, 1320, 1295, 1255, 1210, 1165, 1085, 1060, 980, 945, 850, 815 | 200 | 6.14(s, 1H), 5.61(s, 1H), 4.36(m, 1H), 4.21(d, 2H), 4.12-3.78(m, 2H), 1.96(s, 1H), 1.43(s, 3H), 1.37(s, 3H) |

EXAMPLES 1 to 11

These examples relate to the preparation of anionic living polymers.

The methacrylic acid ester (B-1) was anionically polymerized in the presence of a series of initiators shown in Table 5 in solvents such as xylene, toluene and tetrahydrofuran under polymerization conditions shown in Table 5.

In all cases, anionic polymerization reactions occurred rapidly to produce the aimed anionic living polymers almost quantitatively.

The active terminals of anionic polymers were deactivated with acetic acid equimolar to the respective initiator. And the resulting acetate salts were filtered off. The products were examined by IR and ¹HNMR spectroscopies. In the spectra, no absorption peak due to the conjugated double bonds was observed, and furthermore no change in the absorption patterns due to acetal structure was observed (c.f. Table 7).

It was also confirmed that the absorption spectra of the above products matched exactly with those of poly[2-(1-ethoxyethoxy)ethyl methacrylate] prepared by radical polymerization method.

Further, the molecular weight of the anionic living polymer produced was measured with the use of gel permeation chromatography (GPC), and it was confirmed that the molecular weight distribution is very narrow (c.f. Table 5).

By the same procedures as in the case of ester (B-1), anionic living polymers were obtained from methacrylic acid esters (B-2) to (B-4). The products were subjected to GPC analysis, and the data are summarized in Table 5.

TABLE 5

| | monomer | initiator | reaction temperature (°C.) | reaction time (hrs) | solvent | reaction rate (%) | number average molecular weight objective | number average molecular weight observed | weight average molecular weight observed | dispersion ratio |
|---|---|---|---|---|---|---|---|---|---|---|
| Example 1 | EEMA | KOt-Bu | −78 | 3.0 | o-xylene | 96.5 | 600 | 510 | 590 | 1.15 |
| Example 2 | EEMA | LiOt-Bu | −78 | 3.0 | toluene | 97.0 | 1000 | 990 | 1180 | 1.19 |
| Example 3 | EEMA | KOMe-MeOH | 75 | 5.5 | o-xylene | 93.6 | 1500 | 1560 | 1920 | 1.23 |
| Example | EEMA | t- | −78 | 3.0 | THF | 97.2 | 5000 | 4220 | 6200 | 1.47 |

TABLE 5-continued

| | monomer | initiator | reaction temperature (°C.) | reaction time (hrs) | solvent | reaction rate (%) | number average molecular weight objective | number average molecular weight observed | weight average molecular weight observed | dispersion ratio |
|---|---|---|---|---|---|---|---|---|---|---|
| Example 4 | | BuMgBr | | | | | | | | |
| Example 5 | EEMA | Nabiph | −78 | 3.0 | THF | 96.5 | 3000 | 2740 | 3350 | 1.22 |
| Example 6 | EEMA | LiAlH$_4$ | −78 | 3.0 | THF | 97.3 | 10000 | 8200 | 10600 | 1.29 |
| Example 7 | EEMA | KOt-Bu MeOH | 65 | 3.5 | toluene | 96.9 | 2000 | 1890 | 2360 | 1.25 |
| Example 8 | THPEMA | t-BuMgBr | −78 | 3.0 | THF | 96.2 | 3000 | 2780 | 3590 | 1.29 |
| Example 9 | THPEMA | KOt-Bu | −78 | 3.0 | toluene | 96.8 | 1000 | 1130 | 1330 | 1.18 |
| Example 10 | IBEPMA | KOt-Bu | −78 | 3.0 | o-xylene | 95.9 | 1500 | 1460 | 1840 | 1.26 |
| Example 11 | DOMMA | KOt-Bu | −78 | 3.0 | toluene | 96.1 | 2000 | 2090 | 2820 | 1.35 |

Footnote
KOt-Bu: potassium tert-butoxide
KOMe-MeOH: potassium methoxide-methanol
Nabiph: sodium biphenyl
THF: tetrahydrofuran
LiOt-Bu: lithium-tert-butoxide
t-BuMgBr: tert-butyl magnesium bromide

EXAMPLES 12-20

These examples relate to the preparation of anionic living copolymers. Methacrylic acid ester (B-1) obtained in referential example 1 was anionically copolymerized with n-butyl methacrylate in xylene or toluene in the presence of an anionic initiator either by feeding both monomers into the flask at the same time or by feeding each monomer successively. In all cases, anionic polymerization reactions occurred to produce the aimed anionic living polymers in almost quantitative yields.

Then, the active terminals of these living polymers were deactivated with acetic acid equimolar to anionic initiators, and after filtering off the acetate salts the products were analyzed with IR and $^1$HNMR spectroscopy. The data showed that the absorption peaks due to conjugated double bonds in both methacrylic acid ester (B-1) and n-butyl methacrylate were absent, and that the absorption peaks due to acetal group in methacrylic acid ester (B-1) were unchanged (c.f. Table 7).

Also it was confirmed that the absorption spectra of the above products matched exactly with those of the copolymers prepared by radical polymerization of ester (B-1) and n-butyl methacrylate.

Further, the molecular weights of the anionic copolymers produced were measured by GPC, and it was confirmed that the molecular weight distribution of the copolymers was narrow (c.f. Table 6).

By the same procedures as in the case of ester (B-1), anionic living copolymers were obtained from methacrylic acid esters (B-2) to (B-4). The products were subjected to GPC analysis which provided the results summarized in Table 6.

TABLE 6

| | Example 12 | Example 13 | Example 14 | Example 15 | Example 16 | Example 17 | Example 18 | Example 19 | Example 20 |
|---|---|---|---|---|---|---|---|---|---|
| monomer composition (wt %) | | | | | | | | | |
| EEMA | 30 | 50 | 70 | | | | 20, 20 | 20, 20 | 40 |
| THPEMA | | | | 60 | | | | | |
| IBEPMA | | 50 | | | 30 | | | | |
| DOMMA | | | | | | 40 | | | 30 |
| MMA* | | | 30 | | | | | | |
| n-BMA** | 70 | | | | | | 60 | 60 | |
| EPMA*** | | | | | 70 | | | | |
| AMA**** | | | | | | 60 | | | |
| DMAEMA***** | | | | 40 | | | | | 30 |
| anionic polymerization initiator | KOt-Bu-MeOH | KOt-Bu | KOt-Bu | KOt-Bu | t-BuMgBr | KOt-Bu | KOt-Bu | KOt-Bu-MeOH | KOt-Bu |
| reaction temperature (°C.) | 65 | −78 | −78 | −78 | −78 | −78 | −78 | 65 | −78 |
| reaction time (hrs) | 4.0 | 3.5 | 3.5 | 3.5 | 3.5 | 3.5 | 4.0 | 4.0 | 4.0 |
| solvent | o-xylene | o-xylene | toluene | toluene | toluene | toluene | toluene | o-xylene | toluene |
| footnote | 1 | 2 | 3 | 4 | 5 | 6 | 7 | 7 | 8 |
| reaction rate (%) | 95.9 | 96.8 | 97.4 | 96.3 | 96.0 | 94.2 | 95.0 | 95.7 | 95.5 |
| number average molecular weight objective | 1500 | 1500 | 2000 | 1000 | 5000 | 1000 | 4000 | 2000 | 1500 |
| number average molecular weight observed | 1540 | 1610 | 2180 | 1080 | 6200 | 910 | 3000 | 1890 | 1520 |
| weight average molecular weight | 1890 | 1960 | 2830 | 1300 | 8100 | 1080 | 4500 | 2440 | 2020 |

TABLE 6-continued

|  | Example 12 | Example 13 | Example 14 | Example 15 | Example 16 | Example 17 | Example 18 | Example 19 | Example 20 |
|---|---|---|---|---|---|---|---|---|---|
| observed dispersion ratio | 1.23 | 1.22 | 1.30 | 1.20 | 1.31 | 1.19 | 1.36 | 1.19 | 1.33 |

Footnote
*MMA: methylmethacrylate
**n-BMA: n-butylmethacrylate
***EPMA: 2-ethoxypropylmethacrylate
****AMA: allylmethacrylate
*****DMAEMA: dimethylaminoethylmethacrylate
1. EEEMA (30%) was polymerized first followed by polymerization of n-BMA (70%).
2. EEEMA (50%) was polymerized first followed by polymerization of IBEPMA (50).
3. A mixture of EEEMA (70%) and MMA (30%) was polymerized.
4. A mixture of THPEMA (60%) and DMAEMA (40%) was polymerized.
5. A mixture of IBEPMA and EPMA (70%) was polymerized.
6. A mixture of DOMMA (40%) and AMA (60%) was polymerized.
7. EEEMA (20%) was first polymerized followed by successive polymerization of n-BMA (60%) and EEEMA (20%).
8. EEEMA (40%) was polymerized first followed by successive polymerization DOMMA (30%) and DMAEMA (30%).

EXAMPLE 21

This example relates to preparation of a polymer of a hydroxyl group-containing methacrylic acid ester by hydrolyzing the anionic living polymer obtained in Example 2 in the presence of an acid catalyst.

The anionic living polymer of methacrylic acid ester (B-1) obtained in Example 2 was deactivated with acetic acid equimolar to the initiator, and the resulting acetate salt was filtered off.

The filtrate (a solution of acrylic resin) was hydrolyzed under acidic conditions by repeated washing with a mixture of methanol and 1N aqueous hydrochloric acid solution at room temperature followed by concentration under heating.

The polymers thus produced were subjected to IR and $^1$HNMR spectroscopies. The peaks due to acetal structure disappeared, and instead. the peaks due to hydroxyl group absorption appeared in each spectrogram. Further, the spectra matched with those of poly($\beta$-hydroxyethyl methacrylate) produced by radical polymerization.

EXAMPLE 22

This example relates to the preparation of a copolymer of hydroxyl group-containing methacrylic acid ester and n-butyl methacrylate by hydrolyzing the anionic living copolymer obtained in Example 19 in the presence of an acid catalyst.

First, similarly to the procedure in Example 21, the anionic living copolymer of methacrylic acid ester (B-1) and n-butyl methacrylate was subjected to hydrolysis under acidic conditions.

The copolymer thus obtained was subjected to IR and $^1$HNMR analyses. It was observed that the peaks due to acetal structure disappeared, and instead, the absorption peaks due to hydroxyl groups appeared in each spectrum. Further, the spectra matched with those of $\beta$-hydroxyethyl methacrylate-n-butyl methacrylate copolymer produced by radical polymerization (c.f. Table 7).

TABLE 7

|  |  | Example 1 | Example 12 |
|---|---|---|---|
| IR (neat. cm) | Deactivate of anionic living (co)polymer | 2980, 2950, 2890, 1730, 1450, 1385, 1345, 1250, 1140, 1110, 1090, 1065, 960, 870, 760 | 2950, 2870, 1730, 1460, 1380, 1240, 1140, 1060, 960, 850, 750 |
|  |  | Example 21 | Examples 22 |
|  | (Co)polymer of methacrylic acid ester containing hydroxy group | 3500, 2960, 2900, 1730, 1460, 1395, 1280, 1260, 1170, 1080, 1030, 970, 950, 910, 855, 760 | 3520, 2960, 2940, 2880, 1730, 1460, 1390, 1240, 1160, 1080, 1030, 970, 950, 850, 760 |

TABLE 8

|  | Example 21 | Example 22 |
|---|---|---|
| Polymer obtained | poly ($\beta$-hydroxyethyl methacrylate) | $\beta$-hydroxyethyl methacrylate.n-butyl acrylate copolymer |
| Solvent used | toluene | o-xylene |
| Characteristics |  |  |
| non-volatile content (%) | 80 | 75 |
| Viscosity (25° C. Gardner) | Z | Y |
| OH-value | 340 | 94 |
| number average molecular weight | 650 | 1630 |
| weight average molecular weight | 780 | 1950 |
| dispersion ratio | 1.20 | 1.19 |

Further, the molecular weight of the following polymers was checked by means of GPC and found to be within a narrow distribution range (c.f. Table 8). The polymers were poly($\beta$-hydroxyethyl methacrylate) in Example 21 produced by hydrolysis of the homopolymer of methacrylic acid ester (B-1) and the copolymer of $\beta$-hydroxyethyl methacrylate and n-butyl methacrylate in Example 22 produced by hydrolysis of an anionic living polymer.

APPLICATION EXAMPLE 1

A high solids clear coating composition was prepared by blending poly($\beta$-hydroxyethyl methacrylate) obtained in Example 21 and the adduct of trimethylolpropane with hexamethylenediisocyanate in an equivalent ratio of OH/NCO=1:1.

Then, the composition was applied to mild steel plates treated with bondelite, and baked at 80° C. for 20 min. After being left standing for 7 days at room temperature, the cured film was evaluated by various methods.

The results are summarized in Table 9.

TABLE 9

| | Application example 1 | Application example 2 |
|---|---|---|
| Composition ratio (OH/NCO equivalent ratio) | 1/1 | 1/1 |
| Baking condition (°C./min.) | 80/20 | 80/20 |
| Characteristics of the films obtained | | |
| Appearance of the films | clear and transparent | clear and transparent |
| Solvent resistance | no changed | no changed |
| Moisture resistance | no changed | no changed |
| Acid resistance | no changed | no changed |
| alkali resistance | no changed | no changed |

APPLICATION EXAMPLE 2

The procedure was the same as in the above example except the substitution of poly($\beta$-hydroxyethyl methacrylate) with the copolymer of $\beta$-hydroxyethyl methacrylate and n-butyl methacrylate obtained in Example 22 [the copolymer is referred to polymer (P-1)]. The high solids coating composition thus prepared was evaluated in the same way.

The results are summarized in Table 9. Footnote for Table 9: Solvent Resistance was evaluated by observing surface changes resulting from 50 times repeated rubbing with a piece of xylene-soaked felt loaded with 1 kg weight. Water resistance was evaluated by observing surface changes resulting from immersion in warm water at 50° C. for 24 hours. Acid resistance was evaluated by observing surface changes resulting from immersion in a 5% aqueous solution of sulfuric acid at room temperature for 24 hours. Alkaline resistance was evaluated by observing surface changes resulting from immersion in a 5% aqueous solution of sodium hydroxide at room temperature for 24 hours.

APPLICATION EXAMPLE 3

A high solids clear composition was prepared by blending polymer (P-1) obtained in Example 22 100 g, hexamethoxymethylmelamine 32 g and p-toluenesulfonic acid 0.2 g.

After diluting the composition with a mixed solvent (xylene/n-butanol=70/30) to a viscosity of 40 seconds with Ford Cup #4, the composition was spray-coated on mild steel plates treated with bondelite. Then the coated films was baked at 160° C. for 20 min. to produce cured films having excellent appearance and excellent properties such as solvent resistance, water resistance, acid resistance and alkaline resistance.

The application non-volatile content of the composition was 65%.

APPLICATION EXAMPLE 4

A high solids clear composition was prepared by blending polymer (P-1) with a blocked polyisocyanate prepared by blocking trimethylolpropane-hexamethylenediisocyanate adduct with 2-butanone in an equivalent ratio of OH/blocked NCO=1/1.

After diluting the composition with a mixed solvent (xylene/cyclohexanone=70/30) to a viscosity of 40 seconds with Ford Cup #4, the composition was spray-coated on the above-mentioned substrate, and cured at 160° C. for 30 min. to give cured films having excellent appearance and excellent properties such as water resistance, acid resistance, solvent resistance and alkaline resistance.

The application non-volatile content of the composition was 66%.

APPLICATION EXAMPLE 5

A high solids clear composition was obtained by blending an acetal group-containing polymer [referred to polymer (P-2)] obtained by deactivating the terminals of the anionic living polymer in Preferred Embodiment 19 with trimethylolpropane-hexamethylenediisocyanate adduct in an equivalent ratio of acetal group/NCO=1/1 [the non-volatile content in polymer (P-2) solution was 80%].

After diluting the composition with a mixed solvent (xylene/n-butyl acetate=70/30) to a viscosity of 40 seconds with Ford Cup #4, the composition was spray-coated on the above-mentioned substrate, and cured at 170° C. for 30 min. to give cured film having excellent appearance and excellent properties such as water resistance, solvent resistance, acid resistance and alkaline resistance.

The application non-volatile content of the composition was 75%. No viscosity increase of the diluted composition was observed even after storing for 10 days at room temperature.

APPLICATION EXAMPLE 6

A high solids clear composition was prepared by blending the polymer (P-1) 100 g, hexamethoxymethylmelamine 34 g and p-toluenesulfonic acid 0.6 g.

After diluting the composition with a mixed solvent (xylene/n-butyl acetate=70/30) to a viscosity of 40 seconds with Ford Cup #4, the composition was spray-coated on the above-mentioned substrate, and cured at 170° C. for 30 min. to give cured films having excellent appearance and properties such as solvent resistance, water resistance, acid resistance and alkaline resistance.

The application non-volatile content of the composition was 76%.

APPLICATION EXAMPLE 7

A high solids clear composition was prepared by blending the polymer (P-1), the blocked polyisocyanate used in Application Example 4, and di-2-ethylhexyl phosphate [the eqivalent ratio of acetal group/blocked NCO=1/1, the amount of di-2-ethylhexyl phosphate: 0.5% on total solids of polymer (P-1) and the blocked polyisocyanate].

After diluting the composition with a mixed solvent (xylene/cyclohexanone=70/30) to a viscosity of 40 seconds with Ford Cup #4, the composition was spray coated on the above-mentioned substrate and cured at 170° C. for 30 min. to give cured films having excellent appearance and properties.

The application non-volatile content of the composition was 74%.

What is claimed is:

1. A curable composition comprising an acetal or ketal group-containing methacrylic acid ester polymer produced by deactivation of active terminals of an anionic living polymer of a methacrylic acid ester having at least one acetal- or ketal-blocked hydroxy group, a compound having at least two functional groups reactive with a hydroxyl group in each molecule, and optionally a catalyst.

2. A curable composition according to claim 1, wherein the compound having at least two functional groups reactive with a hydroxyl group in each molecule is at least one compound selected from the group consisting of a polyisocyanate, a blocked polyisocyanate and an amino resin.

3. A curable composition comprising an hydroxyl group-containing methacrylic acid ester polymer produced by hydrolyzing an anionic living polymer of a methacrylic acid ester having at least one acetal or ketal group, and a compound having at least two functional groups reactive with a hydroxyl group in each molecule.

4. A curable composition according to claim 3, wherein the compound having at least two functional groups reactive with a hydroxyl group in each molecule is at least one compound selected from the group consisting of a polyisocyanate, a blocked polyisocyanate and an amino resin.

* * * * *